(12) United States Patent
Wang

(10) Patent No.: US 8,545,546 B2
(45) Date of Patent: Oct. 1, 2013

(54) BIOABSORBABLE SCAFFOLDS MADE FROM COMPOSITES

(75) Inventor: Yunbing Wang, Sunnyvale, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 0 days.

(21) Appl. No.: 13/107,643

(22) Filed: May 13, 2011

(65) Prior Publication Data
US 2012/0290073 A1    Nov. 15, 2012

(51) Int. Cl.
*A61F 2/06* (2013.01)
*A61M 29/00* (2006.01)

(52) U.S. Cl.
USPC ............................. 623/1.15; 606/198

(58) Field of Classification Search
USPC ................ 623/1.11–1.16; 606/194, 198
See application file for complete search history.

(56) References Cited

U.S. PATENT DOCUMENTS

| | | | |
|---|---|---|---|
| 5,624,411 A | 4/1997 | Tuch | |
| 5,713,920 A | 2/1998 | Bezwada et al. | |
| 6,228,954 B1 | 5/2001 | Kaplan et al. | |
| 7,666,342 B2 | 2/2010 | Limon et al. | |
| 7,971,333 B2 | 7/2011 | Gale et al. | |
| 8,002,817 B2 | 8/2011 | Limon | |
| 2004/0193241 A1 | 9/2004 | Stinson | |
| 2007/0231365 A1 | 10/2007 | Wang et al. | |
| 2007/0282426 A1* | 12/2007 | Wang et al. | 623/1.15 |
| 2008/0147165 A1 | 6/2008 | Hossainy et al. | |
| 2008/0177373 A1* | 7/2008 | Huang et al. | 623/1.15 |
| 2009/0012604 A1 | 1/2009 | Schmitz et al. | |
| 2009/0171449 A1* | 7/2009 | Wang | 623/1.34 |
| 2010/0004735 A1 | 1/2010 | Yang et al. | |
| 2011/0022155 A1 | 1/2011 | Wang et al. | |
| 2011/0190871 A1 | 8/2011 | Trollsas et al. | |
| 2011/0190872 A1 | 8/2011 | Anukhin et al. | |

FOREIGN PATENT DOCUMENTS

WO    WO 2007/092417 B1    8/2007

OTHER PUBLICATIONS

Martin et al., "Medical applications of poly-4-hydroxybutyrate: a strong flexible absorbable biomaterial", Biochemical Engineering Journal 16, pp. 97-105 (2003).
"TephaFLEX Absorbable Stents and Stent Coaatings", Tepha medical devices, 1 pg. (2010).
Wang et al., "Polyethylene-Poly(L-lactide) Diblock Copolymers:Synthesis and Compatibilization of Poly(L-lactide)/Polyethylene Blends", J. of Polymer Science, vol. 39, pp. 2755-2786 (2001).

* cited by examiner

*Primary Examiner* — Tuan V Nguyen
(74) *Attorney, Agent, or Firm* — Squire Sanders (US) LLP

(57) ABSTRACT

Bioabsorbable scaffolds made at least in part of a poly(L-lactide)-based composite are disclosed. The composite includes poly(4-hydroxybutyrate) or poly(L-lactide)-b-poly-caprolactone block copolymer, which increases the fracture toughness or fracture resistance of the scaffold. The composite can further include bioceramic particles, L-lactide monomer, or both dispersed throughout the composite. The bioceramic particles improve the radial strength and stiffness of the scaffold. The L-lactide monomer is used to control the absorption rate of the scaffold.

4 Claims, 2 Drawing Sheets

BIOABSORBABLE SCAFFOLDS MADE FROM COMPOSITES

BACKGROUND OF THE INVENTION

1. Field of the Invention

This invention relates polymeric medical devices, in particular, bioabsorbable stents or stent scaffoldings.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, and/or bioerodable materials such as bioabsorbable polymers can be designed to completely erode only after the clinical need for them has ended.

The development of a bioresorbable stent or scaffold could obviate the permanent metal implant in vessel, allow late expansive luminal and vessel remodeling, and leave only healed native vessel tissue after the full absorption of the scaffold. A fully bioabsorbable stent can reduce or eliminate the risk of potential long-term complications and of late thrombosis, facilitate non-invasive diagnostic MRI/CT imaging, allow restoration of normal vasomotion, provide the potential for plaque regression.

However, there are several challenges making a bioabsorbable polymeric stent. These include making a stent with sufficient radial strength, stiffness, toughness or resistance to fracture, and a suitable degradation rate. Additionally, different kinds of treatment with stents have different requirements for the above properties. Another challenge is tailoring bioabsorbable stents to meet these varying requirements.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a stent comprising a scaffolding made from a composite material including: a polymer including poly(L-lactide) (PLLA) as a matrix and poly-4-hydroxybutyrate (P4HB) dispersed throughout the PLLA; and bioceramic particles dispersed throughout the polymer, wherein the bioceramic particles are nanoparticles.

Additional embodiments of the present invention include a method of making a stent comprising a scaffold including: combining PLLA, P4HB, bioceramic particles, and LLA to form a mixture; forming a tube from the mixture using an extruder; and forming a scaffold from the tube, wherein the scaffold comprises 5-15 wt % P4HB and 0.2-1 wt % LLA, and 1-5% bioceramic particles.

Further embodiments of the present invention include a stent comprising a scaffolding made from a composite material including: a polymer including PLLA as a matrix and PLLA-b-PCL or PLLA-co-PCL dispersed throughout the PLLA; and bioceramic particles and LLA dispersed throughout the polymer.

Other embodiments of the present invention include a method of making a stent comprising a scaffolding including: combining PLLA, PLLA-b-PCL or PLLA-co-PCL, bioceramic particles, and LLA to form a mixture; forming a tube from the mixture using an extruder; and forming a scaffold from the tube, wherein the scaffold comprises 5-15 wt % PLLA-b-PCL and 0.2-1 wt % LLA, and 1-5% wt % bioceramic particles.

Additional embodiments of the present invention include a stent comprising a scaffolding made from a composite material including: an inner layer and an outer layer composed of PLLA containing 0 to 1 wt % LLA; a middle layer between the inner layer and the outer layer, the middle layer composed of P4HB with bioceramic particles dispersed throughout the P4HB, wherein the middle layer is 1 to 5 wt % bioceramic particles.

Further embodiments of the present invention include a stent comprising a scaffolding made from a composite material including: an inner layer and an outer layer composed of PLLA; and a middle layer between the inner layer and the outer layer, the middle layer composed of PLLA-b-PCL or PLLA-co-PCL with bioceramic particles and LLA dispersed throughout the PLLA-b-PCL or PLLA-co-PCL, wherein the middle layer is 1 to 5 wt % bioceramic particles and 0.2-1 wt % LLA.

DETAILED DESCRIPTION OF THE INVENTION

The methods described herein are generally applicable to any amorphous or semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
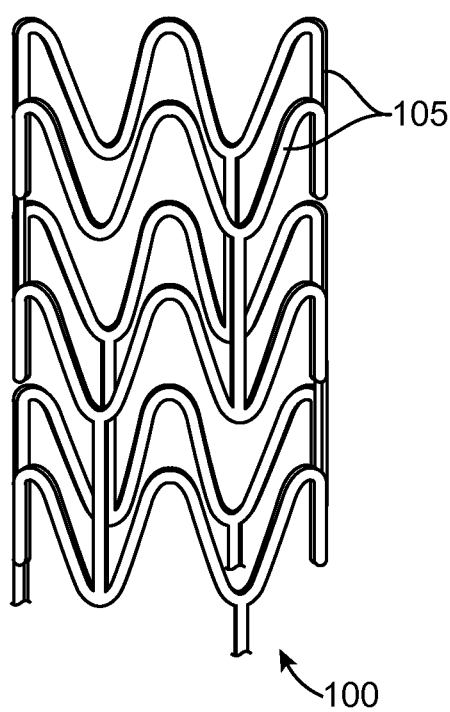
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

A stent of the present invention can be made partially or completely from a biodegradable, bioresorbable, and bioabsorbable polymer. The stent can also be made in part of a biostable polymer. A polymer for use in fabricating stent can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

Bioabsorbable stents can be useful for treatment of various types of bodily lumens including the coronary artery, superficial femoral artery, neural vessels, and the sinuses. In general, these treatments require the stent to provide mechanical support to the vessel for a period of time and then desirably to absorb away and disappear from the implant site. The important properties of a bioabsorbable stent or scaffolding include mechanical and degradation properties. The mechanical requirements include high radial strength, high radial stiffness, and high fracture toughness. The degradation properties include the absorption profile, for example, the change in molecular weight, radial strength, and mass the time. Specific aspects of the absorption profile include the time that the stent maintains radial strength before starting to decrease and the total absorption time or absorption time (complete mass loss from implant site).

A stent scaffolding made from a bioabsorbable polymer may be designed to maintain its radial strength once implanted to provide mechanical support to the vessel and maintain patency of the lumen. The radial strength must be sufficiently high initially to support the lumen at a desired diameter. The period of time that the scaffolding is required or desired to maintain patency depends on the type of treatment, for coronary treatment it is about 3 months. After this time period, the vessel is healed sufficiently to maintain an expanded diameter without support. Therefore, after this time period, the scaffolding may start to lose radial strength due to molecular weight degradation. As the scaffolding degrades further, it starts to lose mechanical integrity and then experiences mass loss and eventually absorbs away completely or there are negligible traces left behind.

Ideally, it is desired that once the stent support is longer needed by the lumen, the bioabsorbable scaffold be absorbed as fast as possible while also meeting all basic safety requirements during its degradation period. Such safety requirements can include a gradual disintegration and resorption that does not allow release of fragments that could cause adverse events such as thrombosis. In this way, the stent scaffolding enables the vessel healing as well as enabling the advantages mentioned herein of a bioabsorbable scaffolding to the greatest extent. It is desirable for a bioabsorbable stent to have an absorption time of about 18 to 26 months for coronary vascular application, of about eighteen months (e.g., 16-20 months) for a peripheral application (e.g., superficial femoral artery (SFA)), 18-24 months for neural applications, and less than a year for nasal applications.

The mechanical requirements of bioabsorbable scaffolding include high radial strength, high stiffness or high modulus, and high fracture toughness. With respect to radial strength and stiffness, a stent should have sufficient radial strength to withstand structural loads, namely radial compressive forces, imposed on the stent so that the stent can supports the walls of a vessel at a selected diameter for a desired time period. A polymeric stent with inadequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a stent by the number and degree of cracks in a scaffolding after use, such as after crimping or deployment. These aspects of the use of the stent involve deformation of various hinge portions of the structural elements of the scaffolding.

Semi-crystalline polymers that are stiff or rigid under biological conditions or conditions within a human body have been shown to be promising for use as a scaffolding material. Specifically, polymers that have a glass transition temperature (Tg) sufficiently above human body temperature which is approximately 37° C., should be stiff or rigid upon implantation. Poly(L-lactide) (PLLA) is attractive as a stent material due to its relatively high strength and a rigidity at human body temperature, about 37° C. As shown in Table 1, PLLA has high strength and tensile modulus compared to other biodegradable polymers. Since it has a glass transition temperature well above human body temperature, it remains stiff and rigid at human body temperature. This property facilitates the ability of a PLLA stent scaffolding to maintain a lumen at or near a deployed diameter without significant recoil (e.g., less than 10%).

PLLA may exhibit a brittle fracture mechanism in which there is little or no plastic deformation prior to failure, as shown by the low elongation to failure of 6% in Table 1. Additionally, the total absorption time of a PLLA is relatively long, as shown by the reported absorption time of 1.5 to 5 years in Table 1.

scaffolds have been shown to be safe and effective for coronary treatment. EuroIntervention. 2010 April; 5(8): 932-8.

However, there is still strong incentive to improve upon PLLA as a stent material not only for coronary applications, but to tailor it for other applications as well. It is important not only to improve the strength of such polymers, but also to improve the fracture toughness to reduce or avoid cracked or broke struts. In particular, a stent should have high resistance to fracture throughout the range of use of a stent, i.e., crimping, delivery, deployment, and during a desired treatment period after deployment.

Therefore, although PLLA may be entirely suitable as a scaffolding material for some applications, such as coronary treatment, it is desirable to address potential deficiencies such as increasing fracture toughness and controlling degradation properties. Additionally, the radial strength and stiffness should be maintained when such deficiencies are addressed. Addressing possible deficiencies may be useful for coronary treatments and especially for treatments in which mechanical demands on the stent are greater than coronary.

For instance, stents implanted in coronary arteries are primarily subjected to radial loads, typically cyclic in nature, which are due to the periodic contraction and expansion of vessels as blood is pumped to and from a beating heart. Thus, in coronary applications, the deformation of the scaffold is normally along the radial direction and such radial deformation is relatively small (less than 5%). Stents implanted in peripheral blood vessels, or blood vessels outside the coronary arteries, e.g., iliac, femoral, popliteal, renal and subclavian arteries, however, must be capable of sustaining both radial forces and crushing or pinching loads. A stent implanted in these vessels are closer to the surface of the body. Therefore, they are particularly vulnerable to bending, crushing or pinching loads, which can partially or completely collapse the stent and thereby block fluid flow in the vessel. Bending deformation can be as high as 20%.

A peripheral stent must take into account the significant differences between these pinching or crushing loads and radial loads, as documented in Duerig, Tolomeo, Wholey,

TABLE 1

Comparison of properties of bioabsorbable polymers. Martin et al., Biochemical Engineering 16 (2003) 97-105.

|  | Tm (° C.) | Tm (° C.) | Tensile Strength (MPa) | Tensile Modulus (MPa) | Elongation at break (%) | Absorption Rate |
|---|---|---|---|---|---|---|
| PLLA | 175 | 65 | 28-50 | 1200-2700 | 6 | 1.5-5 years |
| P4HB | 60 | −51 | 50 | 70 | 1000 | 8-52 weeks |
| PCL | 57 | −62 | 16 | 400 | 80 | 2 years |
| PGA | 225 | 35 | 70 | 6900 | <3 | 6 weeks |
| DL-PLA | Amorphous | 50-53 | 16 | 400 | 80 | 2 years |
| P3HB | 180 | 1 | 36 | 2500 | 3 | 2 years |

PLLA (poly(L-lactide);
P4HB (poly-4-hyroxybutyrate);
PCL (polycaprolactone);
PGA (polyglycolide);
DL-PLA (poly(DL-lactide);
P3HB (poly-3-hydroxybutyrate)

However, the strength and the fracture toughness can be improved through various processing methods (e.g., radial expansion and suitable choice of associated processing parameters). The inventors have also recognized that the absorption rate of PLLA can be controlled by the molecular weight (number average molecular weight, Mn) and L-lactide monomer content. Pre-clinical and clinical studies of PLLA

*Overview of superelastic stent Design*, Min Invas Ther & Allied Technol 9(3/4), pp. 235 246 (2000) and Stoeckel, Pelton, Duerig, *Self-Expanding Nitinol Stents—Material and Design Considerations*, European Radiology (2003). Due to the increased mechanical demands on peripheral stents, it is to be expected and the inventors have recognized that high fracture resistance is of greater significance for peripheral application than coronary applications.

The various embodiments of the present invention include stent scaffolds made from composite materials with PLLA as the base material. The embodiments include blends of PLLA with various blended components that improve the fracture toughness or resistance, modify degradation properties, and maintain radial strength and stiffness. The components which increase the fracture toughness include polymers that have a lower modulus than PLLA, such as poly(4-hydroxybutyrate) (P4HB) and poly(L-lactide)-b-polycaprolactone (PLLA-b-PCL) or poly(L-lactide)-co-polycaprolactone (PLLA-co-PCL). P4HB is a polyhydroxyalkanoate (PHA) and has a faster degradation rate than PLLA, so can also increase the absorption rate of the composite. The components that maintain radial strength include reinforcing agents such as bioceramic particles. L-lactide monomer is a component that is used to control the degradation rate of the composite.

The scaffolds of the present invention can be made completely out of the composite. An exemplary embodiment used in the studies described herein has the stent pattern described in U.S. application Ser. No. 12/447,758 (US 2010/0004735) to Yang & Jow, et al. Other examples of stent patterns suitable for PLLA are found in US 2008/0275537. The cross-section of the struts of the scaffold is 150×150 microns. Such scaffolds may further include a polymer coating which optionally includes a drug. The coating may be conformal (around the perimeter of the scaffold) and may be 2-5 microns thick. In other embodiments described herein, the scaffolds may be made partly out of the composite.

Exemplary stent scaffold patterns for the SFA are disclosed in application Ser. Nos. 13/015,474 and 13/015,488. As compared to coronary stents, a peripheral (SFA) stent scaffold usually has lengths of between about 36 and 40 mm when implanted in the superficial femoral artery, as an example. The scaffold for SFA may have a pre-crimping diameter of between 7-10 mm, or more narrowly 7-8 mm, and can possess a desired pinching stiffness while retaining at least a 80% recoverability from a 50% crush. The scaffold for SFA may have a wall thickness of about 0.008" to 0.014" and configured for being deployed by a non-compliant balloon, e.g., 6.5 mm diameter, from about a 1.8 to 2.2 mm diameter (e.g., 2 mm) crimped profile. The SFA scaffold may be deployed to a diameter of between about 6.5 mm and 7 mm.

One way to increase the fracture toughness of a brittle polymer is to form a polymer-polymer composite of a polymer with low fracture toughness with a polymer with a high fracture toughness under physiological conditions. A "composite" refers generally to a material in which two or more distinct, structurally complementary substances combine to produce structural or functional properties not present in any individual components. The two or more distinct substances may be combinations of different classes of materials such as metals, ceramics, glasses, and polymers. The two or more substances can also be a combination two or more different polymers that form different phases.

In the polymer-polymer composites of the present invention, the low fracture toughness polymer is blended with the high fracture toughness polymer. The higher fracture toughness polymer is at least partially immiscible and forms a plurality of discrete regions or phases that are dispersed within and throughout the low fracture toughness polymer. The low fracture toughness polymer is the matrix, matrix phase, or continuous phase. The discrete or dispersed phase can absorb energy arising from stress imparted to the stent or parts of the stent made from the composite and interrupt fracture propagation to increase the fracture resistance or fracture toughness of the stent. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766. In this way, the highly disperse phase can remain stable, provide uniform energy transfer to interrupt fracture interruption, and thus improved fracture resistance. Insufficient adhesion between phases can result in a dispersed phase that is unstable and thus phase separates further from the matrix resulting in agglomeration.

In certain embodiments, a stent scaffolding is made out of a composite or blend of PLLA and P4HB. As shown in Table 1, P4HB is much more flexible than PLLA with a tensile modulus less than 6% of PLLA. Additionally, the elongation at break of the P4HB is over 150 times that of PLLA. Also, PH4B has a much shorter absorption time. Therefore, a composite of PLLA and P4HB will have an improved fracture toughness and absorption time as compared to PLLA. Additionally, P4HB is particularly advantageous since it is partially miscible with PLLA. Thus, a dispersed phase of P4HB within PLLA is relatively stable once formed.

The Mn of PLLA in these and the other composites described herein can be greater than 60 kDa, 60-70 kDa, 70-80 kDa, 80-90 kDa, 90-100 kDa, or greater than 100 kDa. The Mn of P4HB in these and the other composites described herein can be 40 to 100 kDa.

Although PLLA/P4HB composite is expected to be an improvement over the various material properties of PLLA, stent properties such as radial strength, fracture resistance during crimping and deployment, and absorption behavior do not always bear a direct relationship to material properties. For example, the inventors have recognized that the radial strength and fracture resistance of a stent are a complex function of various factors such as material properties, stent geometry, and morphology. The inventors have found that optimizing the material properties does not necessarily optimize the stent properties.

A bioabsorbable scaffold made from PLLA/P4HB composite can be prepared through extrusion of PLLA and P4HB above their respective melting points and then by forming a tube from the mixture. A tube forming process described in US Pub. No. 2010/00025894. The finished, solidified polymeric tube of PLLA is then be deformed in radial and axial directions by a blow molding process wherein deformation occurs progressively at a predetermined longitudinal speed along the longitudinal axis of the tube. For example, blow molding can be performed as described in U.S. Pub. No. 2009/0001633.

Experimental studies were performed on PLLA/P4HB scaffolds to assess the stent properties. The scaffold pattern used is these studies is described in U.S. application Ser. No. 12/447,758 (US 2010/0004735) to Yang & Jow, et al. The cross-section of the scaffold was 150×150 microns. The Mn of the PLLA in the scaffolds of these studies was about 150 kDa.

The studies included PLLA/P4HB composite scaffoldings that were 15 wt %, and 20 wt %. These scaffolding tubes were prepared through extrusion at 420° F. The extruded PLLA/P4HB tubes could be expanded at a lower temperature and pressure than PLLA. However, in this study, for the sake of comparison, all groups of PLLA/P4HB composites were expanded using the same conditions as the pure PLLA group.

The expansion temperature was 205° F. and the expansion pressure was 110 psi. The tubing diameters for all 3 groups of PLLA/P4HB composites were also the same as the pure PLLA group. All extruded tubes had inside diameter (ID) at 0.20" and outside diameter (OD) at 0.64", while all expanded tubes had an ID at 0.124" and an OD at 0.136.

It was found that all groups of PLLA/P4HB composites scaffolds could be crimped at a lower temperature than PLLA group. However, for the sake of comparison, all three groups were cut, crimped and sterilized at the same conditions, which are used for pure PLLA scaffold preparation.

Table 2 summarizes the results of scaffold functional performance testing for each scaffold group. To compare fracture toughness, all samples were deployed to 3.0 mm first, then 3.5 mm, and then 4.0 mm. The number of broken struts and cracks were recorded for each sample. As shown in Table 3, no broken struts and no cracks greater than 50% strut width were found in the three groups of PLLA/P4HB composite scaffolds, for any of the deployed diameters. However, for the PLLA scaffolds, broken struts were found at 4.0 mm deployment and cracks greater than 50% were found at 3.5 mm deployment. These results suggest that composite scaffolds provide an increase in fracture toughness or resistance when deployed.

TABLE 2

Functional properties of scaffolds made from PLLA/P4HB composites.

| Testing parameter | PLLA | PLLA with 15% P4HB | PLLA with 20% P4HB |
|---|---|---|---|
| Broken struts at 3.0 mm | None | None | None |
| Broken struts at 3.5 mm | None | None | None |
| Broken struts at 4.0 mm | ~12 | None | None |
| Average cracks at 3.5 mm (>50%) | 3.2 ± 2.0 | None | None |
| Radial strength at 3.0 mm | 6.2 ± 0.3 psi | 4.2 ± 0.1 psi | 3.5 ± 0.3 psi |
| Recoil at 3.0 mm | 6.8 ± 1.5% | 8.0 ± 1.2% | 8.1 ± 0.8% |

Table 3 provides the functional properties of the PLLA/P4HB composite with about 20% P4HB group after 3 years of room temperature storage. These scaffolds maintained the fracture resistance with no cracks or broken struts and the radial strength and recoil changed only slightly.

TABLE 3

Functional properties of scaffold after 3 years of room temperature storage.

| Testing Parameter | PLLA with 20% P4HB (T = 3 years) | PLLA with 20% P4HB (T = 0) |
|---|---|---|
| Broken struts at 3.0 mm | None | None |
| Broken struts at 3.5 mm | None | None |
| Broken struts at 4.0 mm | None | None |
| Broken struts at 5.0 mm | None | N/A |
| Average cracks at 3.5 mm (>50%) | None | None |
| Radial strength at 3.0 Mm | 3.3 ± 0.1 psi | 3.5 ± 0.3 psi |
| Recoil at 3.0 mm | 8.5 ± 1.3% | 8.1 ± 0.8% |

The radial strength testing results shown in Table 2 for the two groups of PLLA/P4HB scaffolds exhibited lower radial strength than the pure PLLA group. The radial strength decreases as the percentage of P4HB increased. Therefore, no improvement in fracture toughness was observed as the P4HB was increased, but the radial strength decreased. Recoil testing results in Table 2 showed recoil ranges<10% for all groups of scaffolds made from different PLLA/P4HB composites.

As shown in Table 2, the group with highest content of P4HB (20%) exhibited the lowest radial strength and highest recoil. Data in Table 2 showed that its radial strength and recoil of this group were able to be maintained after 3 years of room temperature storage.

Further embodiments include scaffolds made of composites of PLLA with P4HB or PCL and further including bioceramics, L-lactide monomer, or both. These additional components enable the tailoring of the mechanical and degradation properties for different types of treatments that have different mechanical requirements and different desired degradation behavior.

Peripheral applications may require higher radial strength and faster absorption than that provided by the polymer/polymer composites discussed above. Although, addition of P4HB results in improved fracture toughness of the scaffold, it comes with a decrease in radial strength. Additionally, an application may demand even higher radial strength than provided by pure PLLA or PLLA/P4HB. Also, a faster degradation rate may be desirable for peripheral applications since when structural support is no longer needed, the need for fast absorption is greater than coronary to avoid potential risks associated with the mechanically demanding environment such as broken struts. A polymer such as P4HB increases absorption rate, but increasing concentration come at the expense of radial strength.

In the further embodiments, the composite includes a polymer/polymer composite and one or more additional components that improve selected properties without reduced or no negative impact on other properties. In particular, the polymer-polymer composite may be PLLA blended with a low fracture toughness polymer such as P4HB. The additional components can include bioceramic particles and L-lactide (LLA) monomer. The additional components allow tailoring of the mechanical or degradation properties of a scaffolding for particular treatment. The bioceramic particles allow adjustment of the radial strength or both the radial strength and absorption rate. The LLA allows adjustment of the absorption rate and absorption time independently of the fracture toughness and radial strength and stiffness.

In some embodiments, a polymer-polymer composite further includes bioceramic particles which improve the radial strength of a scaffolding made from the composite. In these embodiments, the bioceramic particles can be mixed, distributed, or dispersed through the polymer-polymer composite or blend. Since bioceramic particles have a higher strength and stiffness than the polymers, the resulting polymer/bioceramic composite material has higher strength and stiffness. A scaffolding made from the resulting composite has a higher radial strength and radial stiffness.

As shown above, the P4HB in a PLLA/P4HB composite increases the fracture toughness of a scaffolding in use, however, the radial strength decreases. The bioceramic particles in the polymer/polymer composite compensate for the loss in radial strength without adverse impact on the fracture toughness or resistance of the scaffolding in use. In fact, bioceramic particles, in addition to improving radial strength of the scaffolding, can improve fracture toughness of the composite and the scaffolding through dispersion of stress and strain over a larger volume.

While the P4HB can increase the absorption rate of the scaffolding which decreases absorption time, the inclusion of bioceramic particles can compensate for the loss of radial strength resulting from a higher composition of P4HB to increase the absorption rate.

Bioceramics can include any ceramic material that is compatible with the human body and can include any type of compatible inorganic material or inorganic/organic hybrid material. Bioceramic materials can include, but are not limited to, alumina, zirconia, apatites, calcium phosphates, silica based glasses, or glass ceramics, and pyrolytic carbons. Bioceramic materials can be bioabsorbable and/or active. A bioceramic is active if it actively takes part in physiological processes. A bioceramic material can also be "inert," meaning that the material does not absorb or degrade under physiological conditions of the human body and does not actively take part in physiological processes.

Illustrative examples of apatites and other calcium phosphates, include, but are not limited hydroxyapatite ($Ca_{10}(PO_4)_6(OH)_2$), fluoroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)6\text{-}5H_2O$), octacalcium phosphate ($Ca_8H_2(PO_4)_6\text{-}5H_2O$), calcium pyrophosphate ($Ca_2P_2O_7\text{-}2H_2O$), tetracalcium phosphate ($Ca_4P_2O_9$), and dicalcium phosphate dehydrate ($CaHPO_4\text{-}2H_2O$). The term bioceramics can also include bioactive glasses that are bioactive glass ceramics composed of compounds such as $SiO_2$, $Na_2O$, $CaO$, and $P_2O_5$.

In some embodiments of a polymer/bioceramic composite, the composite includes bioabsorbable bioceramic particles that modify the absorption rate of the polymer in the composite, and thus, modify the absorption rate of the scaffolding. The bioceramic particles can have acidic degradation by-products ("acidic" bioceramic particles) that can increase the degradation rate of the polymer, which decreases the absorption time of the scaffold. An example cited above of a bioceramic with acidic degradation by-products is calcium sulfate and tricalcium phosphate. The bioceramic particles may have basic degradation products ("basic" bioceramic particles) that can decrease the degradation rate of the polymer, which increases the absorption time of the scaffold. Hydroxyapatite is an example of a bioceramic that has basic absorption products.

In addition, bioceramic particles can have hydrophilic surface groups ("hydrophilic" bioceramic particles), such as hydroxyl groups, which can increase moisture content which increases absorption rate of the polymer and decreases absorption time of the scaffold. An example of a bioceramic particle with surface hydroxyl groups is fluorine mica.

Bioceramic particles may have no basic or acidic degradation by-products or hydrophilic surface groups. Such bioceramic particles, referred to as "neutral" particles, may have little or no effect on the degradation rate or degradation time of a device. Macromol. Mater. Engin. 2003, 288, 203-208. An example of such a material is montmorillonite.

Various sizes of the bioceramic particles may be used in the composite. The bioceramic particles may be nanoparticles which refer to a particles with a characteristic length (e.g., diameter) in the range of about 1 nm to about 1,000 nm. The particles may also have a characteristic length in the range of greater than 1,000 nm and to about 10 microns. Additionally, bioceramic particles can be of various shapes, including but not limited to, spherical and fibers.

Although bioceramic particles are beneficial, they can reach a level that has a detrimental effect on the mechanical properties.

Embodiments can include a scaffold made from a composite including PLLA, P4HB, and bioceramic particles. The P4HB is mixed or dispersed throughout the PLLA. As with other PLLA/P4HB composite blends disclosed herein, the P4HB can be 1-5 wt %, 1-10 wt %, 1-20 wt %, 5-10 wt %, 5-15 wt %, 10-20 wt %, or 20-30 wt % of the composite or of the total weight of the polymer of the composite. As with other bioceramic containing composites disclosed herein, the bioceramic particles can be 1-2 wt %, 1-5 wt %, 1-10 wt %, 5-10 wt %, or greater than 10 wt % of the composite. The balance of the composite may be PLLA or 95-99 wt % PLLA.

Any combination of the disclosed weight percentages of P4HB, bioceramic particles, and PLLA may be used in the composites. The amount of each may depend on the anticipated mechanical demands of the scaffolding upon implantation. For a high degree of fracture resistance, the wt % of P4HB can be increased as necessitated by the application. The bioceramic wt % can then be increased as desired to compensate for the potential loss in radial strength and stiffness due to the P4HB. For example, a composite may have 10-20 wt % P4HB and the 3-5 wt % or 5-10 wt % bioceramic particles.

The absorption rate of the PLLA/P4HB/bioceramic composite can be modified by having acidic, hydrophilic, or basic particles. The use of such particles allows control or adjustment of the absorption rate in addition to or as an alternative to increased P4HB. Thus, the absorption rate is controlled independently or without negative impact on the adjustment of the fracture toughness. In the case of acidic or hydrophilic particles, both the P4HB and acidic or hydrophilic particles cause an increase in the absorption rate of the composite. In the case of basic particles, the basic particles can reduce the increase in absorption rate due to the P4HB. Alternatively, the use of neutral particles allows the control or adjustment of the radial strength with bioceramic particles independently of the absorption rate.

The inventors have found that the absorption rate of PLLA scaffolding and scaffolding absorption time can be controlled in a predictable manner through adjustment of LLA monomer content within the PLLA. The LLA can be mixed or dispersed throughout the polymer of the scaffolding.

In additional embodiments, the scaffolding can be made of a PLLA/P4HB/LLA composite. The LLA increases the absorption rate and decreases the absorption time of a scaffolding. A PLLA/P4HB/LLA composite can have 5-15 wt % P4HB. The LLA can be, as with other LLA-containing composites described herein, greater than 0 and less than 1 wt %, 0.1-1 wt %, 0.2-1 wt % LLA, 0.1-0.2 wt %, 0.2-0.3 wt %, 0.3-0.5 wt %, 0.5-0.7 wt %, or 0.7-1.0 wt % LLA of the composite or of the polymer portion of the composite. The balance of the composite can be PLLA or 95-99% PLLA.

In additional embodiments, the scaffolding can be made of a PLLA/P4HB/bioceramic composite that further includes L-lactide (LLA) monomer. As discussed above, the LLA increases the absorption rate and decreases the absorption time of a scaffolding.

Acidic bioceramic particles can increase the absorption rate of the scaffolding. However, the absorption rate cannot be adjusted independently of radial strength and radial stiffness. The radial strength and stiffness are expected to increase with bioceramic content. The degree of stiffness that is desirable may be limited, for example, an increased degree of stiffness could be detrimental to crush resistance, an important property for SFA applications. Furthermore, P4HB increases the absorption rate of the scaffold, however, the absorption rate cannot be adjusted independently of the radial strength, radial stiffness, and fracture resistance. As shown, as P4HB content increases, the radial strength and stiffness decreases which impacts the ability of a scaffold to support a vessel at a deployed diameter.

A small amount of LLA monomer can be used to adjust the absorption rate and absorption time of a PLLA scaffold or PLLA composite scaffold negligible impact on the radial strength, radial stiffness, and fracture toughness at zero time, i.e., at the time of implantation before any absorption or degradation begins. As LLA content increases, the molecular weight of the PLLA decreases at a faster rate and the radial strength and stiffness start to decrease at an earlier time. A PLLA/P4HB/bioceramic/LLA composite can have an LLA content of 0.1-1 wt % or 0.2-1 wt % of the composite in addition to the compositions of PLLA, P4HB, and bioceramic described above. A PLLA/P4HB/bioceramic/LLA composite can have basic particles, such as hydroxyapatite; acidic particles such as calcium sulfate; and neutral particles such as montmorillonite.

Embodiments can include a scaffolding made from a composite including PLLA, P4HB, bioceramic particles, and LLA. The P4HB can be 1-5 wt %, 1-10 wt %, 1-20 wt %, 5-10 wt %, 5-15 wt %, 10-20 wt %, or 20-30 wt % of the composite or of the total weight of the polymer of the composite. The bioceramic particles can be 1-2 wt %, 1-5 wt %, 1-10 wt %, 5-10 wt %, or greater than 10 wt % of the composite. The LLA content may be 0.1-1 wt % or 0.2-1 wt % of the composite in addition to the compositions of PLLA, P4HB, and bioceramic described above. More narrowly, the LLA may be 0.1-0.3 wt %, 0.1-0.6 wt %, 0.2-0.5 wt %, or 0.2-0.8 wt %. The balance of the composite may be PLLA or 95-99 wt % PLLA.

In further embodiments, a scaffold can be made from a polymer/polymer composite that includes PLLA and polycaprolactone (PCL) to increase its fracture toughness or resistance. The degree of miscibility of PLLA with PCL is much lower than PLLA with P4HB. Therefore, in order to improve the stability of the dispersed PCL phase in the PLLA matrix, the polymer/polymer composite is a block copolymer of PLLA and PCL dispersed in the PLLA matrix, PLLA-b-PCL, or a copolymer PLLA-co-PCL with gradient blocking structure. The PLLA block improves the adhesion of the dispersed phase which is composed mostly or completely of the PCL block. The Mn of the PLLA block can be 10 to 50 kDa. The Mn of the PCL block is 5 to 50 kDa.

As shown in Table 1, the tensile strength of PCL is about a third of that of P4HB. Therefore, for a given content of PCL in the polymer/polymer composite, it is expected that the composite would exhibit a greater drop in radial strength as compared to a PLLA/P4HB composite. However, the tensile modulus of PCL is 5-6 times that of P4HB, so that it is further expected that a PLLA/PLLA-b-PCL composite would exhibit a smaller drop in stiffness as compared to a PLLA/P4HB composite. The elongation at break of P4HB is over 12 time larger than PCL. Therefore, it is expected that the PCL block would improve fracture resistance to a lower degree than P4HB. The absorption time of PCL is significantly longer than P4HB and is closer to that of PLLA, so that PCL is expected to have a much smaller affect on the absorption time on the composite.

The composition of the PLLA/PLLA-b-PCL composite may be, as with other composites including PLLA-b-PCL described herein, 1-5 wt %, 5-15 wt %, 5-10 wt %, or 10-15 wt % PLLA-b-PCL with the balance being PLLA or 95-99 wt % PLLA.

Embodiments of a PLLA/PLLA-b-PCL composite can further include bioceramic particles and LLA. The bioceramic particles can compensate for the drop in the radial strength and stiffness of the polymer/polymer composite due to the PCL block. The absorption rate of the composite can be adjusted through selection of the acid or basic particles. For example, acidic particles can increase the relatively slow absorption rate of the PLLA/PLLA-b-PCL combination.

The absorption rate can be adjusted relatively independently of the mechanical properties through the LLA content of the composite. The LLA can adjust the absorption rate in addition to basic or acidic bioceramic particles. Alternatively, LLA adjusts the absorption rate of the composite when only neutral bioceramic particles are in the composite.

The composition of the PLLA/PLLA-b-PCL/bioceramic/LLA composite may be 5-15 wt % PLLA-b-PCL, 1-5 wt % bioceramic particles, and 0.2-1% LLA. The balance of the composite may be PLLA or 95-99 wt % PLLA. More narrowly, the LLA may be 0.1-0.3 wt %, 0.1-0.6 wt %, 0.2-0.5 wt %, or 0.2-0.8 wt %.

In further embodiments, a scaffold can be made of a PLLA/bioceramic/LLA composite. In these embodiments, the bioceramic particles improve the radial strength and fracture toughness of the composite. The LLA can adjust the absorption rate along with acidic or basic bioceramic particles. Alternatively, the bioceramic particles are neutral and the LLA adjusts the absorption rate. The composition of the composite can be 1-5 wt % bioceramic and 0.1-1 w % or 0.2-1 wt % LLA with the balance being PLLA or 95-99 wt % PLLA.

As discussed above, the scaffolding may be made in part of the composite. In some embodiments, the scaffolding is a sandwich structure with PLLA as an inner layer (inward facing layer or luminal layer) and outer layer (outward facing layer or abluminal layer) and a P4HB/bioceramic composite blend as the middle layer between the inner and outer layers. Since the bioceramic has a much higher strength than P4HB, it is believed that the addition of bioceramic into P4HB system would compensate the loss of radial strength due to the addition of P4HB. Additionally, the inner and outer PLLA layers provide high radial strength to the scaffolding.

Figure 2:
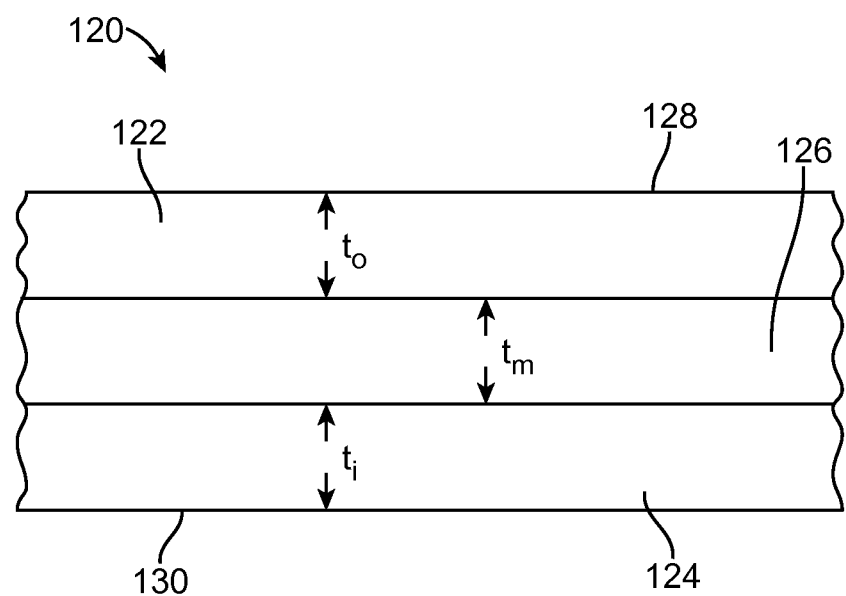
FIG. 2 depicts a portion of a strut of a scaffolding with a view directed at the side wall.

FIG. 2 depicts a portion of a strut 120 of a scaffolding with a view directed at the side wall. FIG. 2 applies to the sandwich structures described herein. Strut 120 has three layers, an outer layer 122 (abluminal layer), an inner layer 124 (luminal layer), and a middle layer 126 between the inner and outer layers. Outer surface 128 faces vessel walls and inner surface 130 faces the lumen of a vessel when the scaffolding is implanted Inner layer 122 has a thickness ti, outer layer 124 has a thickness to, and middle layer 126 has a thickness tm. The outer and inner layers may be composed of PLLA, or as discussed below, PLLA/LLA. The middle layer may be composed of the composite.

The thickness of the inner, outer, and middle layers may be the same. Alternatively, the thickness of the inner and outer layers may be the same and the thickness of the middle layer be different, either thicker or thinner than the inner and outer layers. The thickness of the middle composite layer may be varied depending on the mechanical demands of the stent. A scaffolding that requires greater flexibility, such as for an SFA application, may have a middle layer thickness the same as or greater than the inner and outer layers, for example, 10-20% greater than the inner or outer layer. A scaffolding that requires greater stiffness may have a middle layer thickness less than the inner or outer layer thickness, for example, 10-20% less than the inner or outer layer.

The absorption time of the scaffold can be controlled by using basic or acidic particles. Acidic particles can be used to accelerate absorption rate of the P4HB and PLLA and decrease the absorption time of the entire scaffold.

The P4HB/bioceramic composite layer can be 1-5% bioceramic particles and remainder being P4HB and optionally small amounts of impurities (less than 1%) or other additives. The scaffold may be prepared from a multi-layer tube with a middle layer made of the composite and the outer layers made from PLLA. The multi-layer tube may be made through extrusion. In addition, the scaffold can also include more than 3 layers, e.g., 4 to 10 layers. For example, PLLA layers may alternate with composite layers.

In other embodiments, the scaffolding is a sandwich structure with PLLA as inner layer and a PLLA-b-PCL/bioceramic/LLA composite blend as the middle layer between the inner and outer layers. In these embodiments, the PLLA-b-PCL increases the fracture toughness of scaffolding. The LLA increases the absorption rate, while the bioceramic particles increase the radial strength, and therefore, compensate for any potential loss of radial strength in the middle layer due to the PCL block. Other materials such as PLLA-co-PCL, PLLA-b-PTMC, PLLC-co-PTMC, or PLLA-b-PDO may be substituted for the PLLA-b-PCL. The middle layer may have 1-5% bioceramic particles, 0.2-1% LLA and remainder being PLLA-b-PCL. In addition, the scaffold can also include more than 3 layers, e.g., 4 to 10 layers. For example, PLLA layers may alternate with composite layers.

In another embodiment, the scaffolding is a sandwich structure with a PLLA/LLA mixture as the inner and outer layers and P4HB or PLLA-b-PCL/LLA as the middle layer. In this approach, the fracture toughness is increased by the P4HB or PCL block. In the latter case, the absorption rate would be accelerated by the LLA. The middle layer may be PLLA-b-PCL containing 0.2 to 1% LLA and inner and outer layers may also have 0.2-1% LLA. It is expected that the radial strength may decrease due to the addition of the PCL.

The embodiments of the present invention are directed to composite materials for a scaffolding based on PLLA, however, a composite can include or be based on poly(D-lactide) (PDLA), polyglycolide (PGA), and poly(L-lactide-co-glycolide) (PLGA). The PLGA have a mole % of GA between 5-15 mol %. The PLGA can have a mole % of (LA:GA) of 85:15 (or a range of 82:18 to 88:12), 95:5 (or a range of 93:7 to 97:3), or commercially available PLGA products identified being 85:15 or 95:5 PLGA.

It is believed that SFA scaffolds, such as those disclosed above, made from some or all of the composites disclosed herein may be deployed from a crimped diameter (e.g., 1.8 to 2.2 mm or 2 mm) to a diameter of 6.5 to 7 mm with no broken struts and no cracks. Additionally, such scaffolds may have a radial strength, as measured by techniques described herein an in cited applications, of greater than about 0.3 N/mm, or between about 0.32 and 0.68 N/mm, and a radial stiffness of greater than about 0.5 N/mm or between about 0.54 N/mm and 1.2 N/mm.

The fabrication methods of a bioabsorbable stents described herein can include the following steps:
 (1) forming a polymeric tube using extrusion,
 (2) radially deforming the formed tube,
 (3) forming a stent scaffolding from the deformed tube by laser machining a stent pattern in the deformed tube with laser cutting,
 (4) optionally forming a therapeutic coating over the scaffolding,
 (5) crimping the stent over a delivery balloon, and
 (6) sterilization with election-beam (E-Beam) radiation.

In the extrusion step, a polymer is processed in an extruder above its melting temperature. The components of the composites described above can be combined and mixed in the extruder. The bioceramic particles, the LLA, or both can be added to the polymer and mixed in the extruder. Alternatively, the bioceramic particles, LLA, or both may be mixed in a separate step with some of the polymer to form a mixture having higher concentration(s) than the final concentration(s) of the product. The high concentration polymer mixture can then be added to additional polymer in the extruder to form a composite tube.

In step (2) above, the extruded tube may be radially deformed to increase the radial strength of the tube, and thus, the finished stent. The increase in strength reduces the thickness of the struts required to support a lumen with the stent when expanded at an implant site. In exemplary embodiments, the strut thickness can be 100-200 microns, or more narrowly, 120-180, 130-170, or 140-160 microns.

Detailed discussion of the manufacturing process of a bioabsorbable stent can be found elsewhere, e.g., U.S. Patent Publication No. 20070283552, which is incorporated by reference herein.

A "gradient block structure" refers to copolymer structure in which there is a gradual change in the junction(s) between the blocks from that of repeat units of one type (A) and to that of the other (B). A gradient block structure may be represented as:

-AAABAABABBABBB-.

All "A-co-" copolymers referred to herein can refer to gradient block structure copolymers, random copolymers, or alternating copolymers.

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress-strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

EXAMPLES

1. Scaffold Preparation from PLLA/P4HB/Bioceramic Composite

Step 1: PLLA/P4HB/bioceramic composite preparation

In this experiment, a PLLA/P4HB/bioceramic composite with P4HB and bioceramic content at 10%, 2%, is prepared through twin screw extrusion at 420° F. with screw speed at 50 rpm.

Step 2: Scaffold preparation

2a). Tubing extrusion and expansion: PLLA/P4HB/bioceramic composite is extruded and expanded. The temperature for extrusion is set at 420° F., the expansion temperature is 205° F. and the expansion pressure is 110 psi. The extruded tube of PLLA/P4HB/bioceramic has an ID at 0.20" and OD at 0.64", while the expanded tube has ID at 0.124" and OD at 0.136".

2b). The expanded PLLA/P4HB/bioceramic composite tube is laser cut, crimped, and sterilized for testing.

2. Scaffold Preparation from PLLA/PLLA-b-PCL/Bioceramic/LLA Composite

Step 1: PLLA/PLLA-b-PCL/bioceramic/LLA composite preparation

In this experiment, PLLA/PLLA-b-PCL/bioceramic/LLA composite with PLLA-b-PCL, bioceramic and LLA content at 10%, 2%, and 0.5% is prepared through twin screw extrusion at 420° F. with screw speed at 50 rpm.

Step 2: Scaffold preparation

2a). Tubing extrusion and expansion: PLLA/PLLA-b-PCL/bioceramic/LLA composite is extruded and expanded. The temperature for extrusion is 420° F., the expansion temperature is 205° F. and the expansion pressure is 110 psi. The extruded tube of PLLA/PLLA-b-PCL/bioceramic/LLA has ID at 0.20" and OD at 0.64", while the expanded tube has ID at 0.124" and OD at 0.136".

2b). The expanded PLLA/PLLA-b-PCL/bioceramic/LLA composite tube is laser cut, crimped and sterilized.

2. Scaffold Preparation of Sandwich Structure Scaffold with PLLA as Inner and Outer Layer and P4HB/Bioceramic Composite as Middle Layer Step 1: P4HB/bioceramic composite preparation P4HB/bioceramic composite with bioceramic content at 1-5% is prepared with twin screw extrusion at 220° F. with screw speed at 30 rpm.

Step 2: Scaffold preparation

2a). Tubing extrusion and expansion: sandwich structure scaffold with PLLA as inner and outer layer and P4HB/bioceramic composite as middle layer is prepared through coextrusion of PLLA and P4HB/bioceramic composite. Then the extruded tube is expanded to further increase its strength and toughness. The temperature for extrusion is set at 420° F., the expansion temperature is 205° F. and the expansion pressure is 110 psi. The extruded tube diameter has ID at 0.20" and OD at 0.64", while the expanded tube has ID at 0.124" and OD at 0.136". The thickness of three layers is the same.

2b). The expanded tube is laser cut, crimped and sterilized.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a scaffolding made from a composite material including:
   an inner layer and an outer layer composed of PLLA containing 0 to 1 wt % LLA;
   a middle layer between the inner layer and the outer layer, the middle layer composed of P4HB with bioceramic particles dispersed throughout the P4HB, wherein the middle layer is 1 to 5 wt % bioceramic particles.

2. The stent of claim 1, wherein the bioceramic particles are calcium sulfate particles.

3. A stent comprising a scaffolding made from a composite material including:
   an inner layer and an outer layer composed of PLLA; and
   a middle layer between the inner layer and the outer layer, the middle layer composed of PLLA-b-PCL or PLLA-co-PCL with bioceramic particles and LLA dispersed throughout the PLLA-b-PCL or PLLA-co-PCL, wherein the middle layer is 1 to 5 wt % bioceramic particles and 0.2-1 wt % LLA.

4. The stent of claim 3, wherein the bioceramic particles are calcium sulfate particles.

* * * * *